United States Patent
Ni et al.

(10) Patent No.: US 9,896,477 B2
(45) Date of Patent: Feb. 20, 2018

(54) LIMONIN EXTRACTION METHOD

(71) Applicant: JIMEI UNIVERSITY, Xiamen, Fujian Province (CN)

(72) Inventors: Hui Ni, Xiamen (CN); Huinong Cai, Xiamen (CN); Yuanfan Yang, Xiamen (CN); Qiufen Gao, Xiamen (CN); Feng Chen, Xiamen (CN); Xiping Du, Xiamen (CN); Gaoling Huang, Xiamen (CN); Ling Wu, Xiamen (CN); Anfeng Xiao, Xiamen (CN)

(73) Assignee: JIMEI UNIVERSITY, Xiamen, Fujian Province (CN)

( * ) Notice: Subject to any disclaimer, the term of this patent is extended or adjusted under 35 U.S.C. 154(b) by 10 days.

(21) Appl. No.: 15/302,983

(22) PCT Filed: Apr. 30, 2015

(86) PCT No.: PCT/CN2015/000299
§ 371 (c)(1),
(2) Date: Oct. 8, 2016

(87) PCT Pub. No.: WO2015/188611
PCT Pub. Date: Dec. 17, 2015

(65) Prior Publication Data
US 2017/0029460 A1    Feb. 2, 2017

(30) Foreign Application Priority Data

Jun. 12, 2014  (CN) .......................... 2014 1 0259115

(51) Int. Cl.
*A23L 33/105* (2016.01)
*C07J 73/00* (2006.01)

(52) U.S. Cl.
CPC ............. *C07J 73/00* (2013.01); *A23L 33/105* (2016.08); *C07J 73/008* (2013.01); *A23V 2002/00* (2013.01)

(58) Field of Classification Search
CPC ..................................................... A23L 33/105
See application file for complete search history.

*Primary Examiner* — Noble E Jarrell
*Assistant Examiner* — John S Kenyon
(74) *Attorney, Agent, or Firm* — PROI Intellectual Property US

(57) ABSTRACT

A limonin extraction method, comprising the following steps: step one, raw material extracting or juicing: directly soaking raw material in water or using a presser to directly juice the raw material to obtain the extract; step two, adding salt and adjusting pH: adding a sulfate solid material or saturated sulfate solution to the extract; adjusting pH to 3-7; step three, heating and preserving heat: heating to 20° C.-100° C. and keeping at the temperature for 10 minutes-110 minutes; step four, centrifuging: centrifuging for 10 minutes at a rotational speed of 2500×g, and obtaining limonin precipitation. Compared with a traditional method, the raw material in the present invention can directly use the extract liquid or juicing liquid without drying, and recover most limonin in water using a precipitation method without complicated apparatus, and is easy to operate and has a low process cost.

5 Claims, No Drawings

LIMONIN EXTRACTION METHOD

CROSS REFERENCE TO RELATED APPLICATIONS

The present application is the US national stage of International Patent Application PCT/CN2015/000299 filed on Apr. 30, 2015, which, in turn, claims priority to Chinese Patent Application CN 201410259115.2 filed on Jun. 12, 2014.

TECHNICAL FIELD

The present disclosure relates to a limonin extraction method, and particularly relates to a limonin extraction method by precipitation.

BACKGROUND

Limonin analogues are highly oxidized tetracyclic triterpenoids mainly existing in rutaceae and meliaceae plants. People have successively separated different limonin analogues since Bemay (1841) separated limonin for the first time, and have separated more than 300 limonin analogues from citrus plants and hybrid plants thereof at present.

In recent decades, people have found that limonin analogues in citrus fruits have many biological functions: antimalarial, antibacterial, anti-inflammatory, analgesic, insecticidal functions, etc., can effectively prevent pathogenic bacteria from encroaching on animal bodies, can expel parasites from animal bodies; can stimulate the activity of glutathione transferase, a main detoxification enzyme in vivo, and have very strong antitumor activity. Pesticide prepared from limonin analogues at a certain concentration is a natural, non-toxic and desired biopesticide with good insecticidal efficacy. Embedded limonin analogues can be very widely used as functional food additives. Japan has had a patent for producing functional food using limonin analogues. Limonin analogues also have activities, such as antioxidation, antitumor, exciting central nervous system, etc., have significant importance for the industries, such as human medicine, food, agricultural production, etc., and are bioactive substances with very high development value.

Limonin is an electrically neutral triterpenoid dilactone compound with a molecular formula of $C_{26}H_{30}O_8$ and with a hydrophobic structure, is easily soluble in ester-soluble organic solvent, and is hardly soluble in water. The traditional limonin extraction method degreases and extracts dried raw materials with an organic solvent. The frequently used extraction method generally extracts limonin using the solubility of limonin in the extract and mainly using the solvent of dichloromethane, hexane, methanol, acetone, isopropanol, etc. At present, the widely used degreasing solvents include petroleum ether, ethyl ether, ethanol and methanol. The traditional method is expensive and time-consuming, and does not facilitate realizing industrialized production of limonin preparation.

Besides, a part of limonin is soluble in water solution in the form of limonin A-ring lactone, and is therefore difficult to be separated. Some researchers adsorb limonin in resin from an aqueous solution, and then elute adsorbed limonin with an organic solvent, which also needs to use a lot of organic solvent, needs recovery of the organic solvent, and has high process cost. For this reason, the inventor has researched and designed a limonin extraction method, thereby resulting in the present application.

SUMMARY

The present disclosure aims to provide a limonin extraction method using sulfate precipitation method, so as to achieve the purpose of rapid and efficient extraction of limonin at low cost.

To achieve the above purpose, the present disclosure provides a technical solution to solve the technical problem as follows:

A limonin extraction method, including the following steps:

step one, raw material extracting or juicing: directly soaking raw material in water or using a presser to directly juice the raw material to obtain an extract;

step two, adding salt and adjusting pH: adding a sulfate solid material or saturated sulfate solution to the extract; adjusting pH to 3-7;

step three, heating and preserving heat: heating to 20 to 100° C. and keeping at the temperature for 10 minutes to 110 minutes; and step four, centrifuging: obtaining limonin precipitation by centrifugation at a rotational speed of 2500×g for 10 minutes.

According to a preferred embodiment, in the step two, the sulfate is ammonium sulfate, magnesium sulfate, sodium sulfate and potassium sulfate.

According to a preferred embodiment, in the step two, the pH is adjusted to 4-6.

According to a preferred embodiment, in the step three, the heating temperature is 60-80° C.

According to a preferred embodiment, in the step three, the heating time is 10 minutes.

The present disclosure adopts the above technical solution, namely directly extracting raw material with water or juicing the raw material by pressing, adding certain amount of sulfate solid or saturated sulfate solution, adjusting pH and temperature to precipitate limonin, and obtaining high concentration of limonin precipitation by centrifugation. Compared with a traditional method, the present disclosure can directly use the extract or juice of the raw material without drying, and recover most limonin in water using a precipitation method without complicated devices, is easy tooperate, and has low process cost.

DESCRIPTION OF THE EMBODIMENTS

The embodiments of the present disclosure illustrate the process of the present disclosure with limonin extraction from pummelos. However, the present disclosure is not only limited to limonin extraction from pummelos and other citrus fruits, but also applicable to extraction from plant materials rich in limonin, such as neem, African mahogany, etc. Therefore, the method in the embodiments of the present disclosure is a general method for extracting limonin from plants containing limonin.

The present disclosure detects the limonin content using Waters e2695 high performance liquid chromatograph (Waters e2695 Separations Module, Waters 2489 UV/Visible Detector, Empower 2 software) and Symmetry reversed phase C18 column (3.0×250 mm, 5.0 μm) under specific chromatographic detection conditions of: (1) detecting limonin at a wavelength of $\lambda$=210 nm; (2) flow rate: 0.5 ml/minute, column temperature: 35° C., sample injection volume: 20 μL; (3) gradient elution conditions (A: ultrapure water, B: acetonitrile): 0-4 min 95% A; 4-14 min 95-60% A; 14-16 min 60% A; 16-4 min 60-30% A; 24-28 min 30-95% A; 28-32 min 95% A. Qualitative analysis is based on retention time, and quantitative analysis is based on peak area. Limonin extraction yield is calculated as per the following equation:

$$\text{Limonin extraction yield (\%)} = A2/A1*100$$

wherein:
A1 indicates total content of limonin in pummelo extract (μg/mL), and
A2 indicates content of limonin in precipitation collected after centrifugation (μg/mL).

Embodiment 1

Step one, pressing pummelo to obtain an extract. Limonin content in the extract was detected to be 84.21 μg/mL;

Step two, preparing 80% saturated ammonium sulfate solution. 1 mL of 80% saturated ammonium sulfate solution was fully mixed with 4 mL of the pummelo extract to obtain a pummelo extract with sulfate ion concentration of 0.85 mol/L and at a pH of 4.17;

Step three, keeping at 50° C. for 90 minutes, and then heating at 100° C. for 20 minutes; and Step four, centrifuging at a rotational speed of 2500×g for 10 minutes.

The limonin content in the precipitation redissolved in 4 mL of 60% acetonitrile was detected to be 6.29 μg/mL. The total extraction yield of limonin was calculated to be 7.47%.

Embodiment 2

Step one, pressing pummelo to obtain an extract. Limonin content in the extract was detected to be 85.87 μg/mL;

Step two, preparing 100% saturated ammonium sulfate solution. 1 mL of 100% saturated ammonium sulfate solution was fully mixed with 4 mL of the pummelo extract to obtain a pummelo extract with sulfate ion concentration of 1.07 mol/L and at a pH of 4.14;

Step three, keeping at 50° C. for 90 minutes, and then heating at 100° C. for 20 minutes; and Step four, centrifuging at a rotational speed of 2500×g for 10 minutes.

The limonin content in the precipitation redissolved in 4 mL of 60% acetonitrile was detected to be 22.92 μg/mL. The total extraction yield of limonin was calculated to be 26.69%.

According to Embodiment 1 and Embodiment 2, the extraction yield of limonin is proportional to the concentration of ammonium sulfate in juice.

Embodiment 3

Step one, directly soaking pummelo in tap water to obtain an extract. Limonin content in the pummelo extract adjusted with sodium hydrogen phosphate to a pH of 4 was detected to be 60.11 μg/mL;

Step two, preparing 100% saturated ammonium sulfate solution. 1 mL of 100% saturated ammonium sulfate solution was fully mixed with 4 mL of the pummelo extract to obtain a pummelo extract with sulfate ion concentration of 1.07 mol/L and at a pH of 3.98;

Step three, heating at 100° C. for 20 minutes; and

Step four, centrifuging at a rotational speed of 2500×g for 10 minutes.

The limonin content in the precipitation redissolved in 4 mL of 60% acetonitrile was detected to be 17.25 μg/mL. The extraction yield of limonin was calculated to be 28.70%.

Embodiment 4

Step one, directly soaking pummelo in tap water to obtain an extract. Limonin content in the pummelo extract adjusted with sodium hydrogen phosphate to a pH of 6 was detected to be 60.11 μg/mL;

Step two, preparing 100% saturated ammonium sulfate solution. 1 mL of 100% saturated ammonium sulfate solution was fully mixed with 4 mL of the pummelo extract to obtain a pummelo extract with sulfate ion concentration of 1.07 mol/L and at a pH of 5.97;

Step three, heating at 100° C. for 20 minutes; and

Step four, centrifuging at a rotational speed of 2500×g for 10 minutes.

The limonin content in the precipitation redissolved in 4 mL of 60% acetonitrile was detected to be 38.89 μg/mL. The extraction yield of limonin was calculated to be 26.49%.

Embodiment 5

Step one, pressing pummelo to obtain an extract. Limonin content in the extract was detected to be 87.44 μg/mL;

Step two, preparing 100% saturated ammonium sulfate solution. 1 mL of 100% saturated ammonium sulfate solution was fully mixed with 4 mL of the pummelo extract to obtain a pummelo extract with sulfate ion concentration of 1.07 mol/L and at a pH of 4.14;

Step three, heating at 100° C. for 20 minutes; and

Step four, centrifuging at a rotational speed of 2500×g for 10 minutes.

The limonin content in the precipitation redissolved in 4 mL of 60% acetonitrile was detected to be 36.37 μg/mL. The extraction yield of limonin was calculated to be 41.60%.

Embodiment 6

Step one, pressing pummelo to obtain an extract. Limonin content in the extract was detected to be 91.07 μg/mL;

Step two, preparing 100% saturated ammonium sulfate solution. 1 mL of 100% saturated ammonium sulfate solution was fully mixed with 4 mL of the pummelo extract to obtain a pummelo extract with sulfate ion concentration of 1.07 mol/L and at a pH of 4.15;

Step three, heating at 100° C. for 30 minutes; and

Step four, centrifuging at a rotational speed of 2500×g for 10 minutes.

The limonin content in the precipitation redissolved in 4 mL of 60% acetonitrile was detected to be 39.06 μg/mL. The extraction yield of limonin was calculated to be 42.90%.

Embodiment 7

Step one, pressing pummelo to obtain an extract. Limonin content in the extract was detected to be 57.28 μg/mL;

Step two, preparing 100% saturated ammonium sulfate solution. 1 mL of 100% saturated ammonium sulfate solution was fully mixed with 4 mL of the pummelo extract to obtain a pummelo extract with sulfate ion concentration of 1.07 mol/L and at a pH of 4.14;

Step three, heating at 60° C. for 15 minutes; and

Step four, centrifuging at a rotational speed of 2500×g for 10 minutes.

The limonin content in the precipitation redissolved in 4 mL of 60% acetonitrile was detected to be 36.48 μg/mL. The extraction yield of limonin was calculated to be 63.68%.

Embodiment 8

Step one, pressing pummelo to obtain an extract. Limonin content in the extract was detected to be 80.11 μg/mL;

Step two, adding ammonium sulfate solid to 4 mL of the pummelo extract to obtain a pummelo extract with ammonium sulfate concentration of 5.35 mol/L and at a pH of 3.99;

Step three, heating at 70° C. for 20 minutes; and

Step four, centrifuging at a rotational speed of 2500×g for 10 minutes.

The limonin content in the precipitation redissolved in 4 mL of 60% acetonitrile was detected to be 57.82 μg/mL. The extraction yield of limonin was calculated to be 72.18%.

Embodiment 9

Step one, pressing pummelo to obtain an extract. Limonin content in the extract was detected to be 80.50 μg/mL;

Step two, adding ammonium sulfate solid to 4 mL of the pummelo extract to obtain a pummelo extract with ammonium sulfate concentration of 5.35 mol/L and at a pH of 3.13;

Step three, heating at 80° C. for 20 minutes; and

Step four, centrifuging at a rotational speed of 2500×g for 10 minutes.

The limonin content in the precipitation redissolved in 4 mL of 60% acetonitrile was detected to be 55.50 μg/mL. The extraction yield of limonin was calculated to be 68.94%.

Compared with a traditional method, the above methods of the present disclosure can directly use the extract or juice of the raw material without drying, and recover most limonin in water using a precipitation method without complicated devices, is easy to operate, and has low process cost.

The above description only provides preferred embodiments of the present disclosure, and is not intended to limit the scope of embodiments of the present disclosure. That is, all equivalent variations and modifications made within the scope of the present disclosure and the contents of the Description shall fall within the scope of the present disclosure.

What is claimed is:

1. A limonin extraction method, comprising the following steps:
    step one, raw material extracting or juicing: directly soaking raw material in water or using a presser to directly juice the raw material to obtain an extract;
    step two, adding salt and adjusting pH: adding a sulfate solid material to the extract; and adjusting pH to 3-7;
    step three, heating and preserving heat: heating to 20 to 100° C. and keeping at the temperature for 10 minutes to 110 minutes; and
    step four, centrifuging: obtaining limonin precipitation by centrifugation at a rotational speed of 2500×g for 10 minutes.

2. A limonin extraction method according to claim 1, wherein, in the step two, the sulfate is ammonium sulfate, magnesium sulfate, sodium sulfate or potassium sulfate.

3. A limonin extraction method according to claim 1, wherein, in the step two, the pH is adjusted to 4-6.

4. A limonin extraction method according to claim 1, wherein, in the step three, the heating temperature is 60-80° C.

5. A limonin extraction method according to claim 1, wherein, in the step three, the heating time is 10 minutes.

* * * * *